United States Patent
Park (10) Patent No.: US 8,741,964 B2
(45) Date of Patent: Jun. 3, 2014

(54) USES OF NONENAL

(75) Inventor: Tae Sun Park, Seoul (KR)

(73) Assignee: Industry-Academic Cooperation Foundation, Yonsei University, Seoul (KR)

( * ) Notice: Subject to any disclaimer, the term of this patent is extended or adjusted under 35 U.S.C. 154(b) by 44 days.

(21) Appl. No.: 13/484,241

(22) Filed: May 30, 2012

(65) Prior Publication Data

US 2012/0309848 A1 Dec. 6, 2012

(30) Foreign Application Priority Data

Jun. 1, 2011 (KR) .................. 10-2011-0052753

(51) Int. Cl.
*A61K 31/11* (2006.01)
(52) U.S. Cl.
USPC ........................................... 514/703
(58) Field of Classification Search
USPC ........................................... 514/703
See application file for complete search history.

(56) References Cited

PUBLICATIONS

Angel Hernandez-Hernandez et al., "Structural characteristics of a lipid peroxidation product, trans-2-nonenal, that favour inhibition of membrane-associated phosphotyrosine phosphatase activity", Biochimica et Biophysica Acta (vol. 1726, No. 3, pp. 317-325, 2005).

*Primary Examiner* — Kevin E Weddington
(74) *Attorney, Agent, or Firm* — Lee, Hong, Degerman, Kang & Waimey (57) ABSTRACT

The present invention relates to a method for preventing or treating dyslipidemia or fatty liver, comprising: administering to a mammalian subject in need thereof a therapeutically effective amount of a composition comprising nonenal. The present composition containing nonenal as an active ingredient is very effective in preventing or treating obesity, diabetes, dyslipidemia, fatty liver or insulin resistance syndrome (preferably, dyslipidemia or fatty liver, more preferably hyperlipidemia or fatty liver). The composition of the present invention useful as pharmaceuticals compositions or functional food compositions has therapeutic efficacies for obesity, diabetes, hyperlipidemia or fatty liver, and also induces significant decrease in fasting glucose level and blood insulin level to improve type 2 diabetes, insulin resistance and related metabolic disorders.

10 Claims, 10 Drawing Sheets

USES OF NONENAL

CROSS-REFERENCE TO RELATED APPLICATIONS

Pursuant to 35 U.S.C. §119 (a), this application claims the benefit of earlier filing date and right of priority to Korean Patent Application No. 10-2011-0052753 filed on Jun. 1, 2011, the contents of which are hereby incorporated by reference in their entirety.

BACKGROUND OF THE INVENTION

1. Field of the Invention

The present invention relates to novel uses of nonenal, in particular, a method for preventing or treating dyslipidemia or fatty liver.

2. Background of Technique

At present, 1.7 billion people amounting to about 25% of the world population are overweight (BMI>25) and more than 300 million people including 120 million in the US, Europe and Japan are classified as obese (BMI>30). Among the OECD countries, the US has the highest obesity rate of 31% of population, followed by Mexico (24%), England (23%), Greece (22%), Australia (22%), New Zealand (21%), Hungary (19%), Canada (14%), Spain (13%), Ireland (13%), Germany (13%), Portugal (13%), Finland (13%), Turkey (12%) and Belgium (12%). The number of obese people in China is 70 million and the body weight control-related market is expanding, estimated at about 10 billion yuan. Childhood obesity is also increasing rapidly worldwide, with 1 in 5 children being obese. As such, childhood obesity is becoming a serious social issue. Since childhood obesity is the main cause of the life style diseases including diabetes, hypertension, stroke, etc. with increased blood cholesterol and triglyceride level, 80% or more of obese children are likely to become obese adults. Further, since increased fat stimulates secretion of sex hormones and induces early adolescence, childhood obesity may cause growth problems. Also, it negatively affects blood circulation and nourishment.

According to statistics of Korea Institute for Health and Social Affairs, the socioeconomic loss caused by obesity and obesity-related complications in 2006 is estimated at 2.1 trillion won including medical cost and indirect cost such as loss of earning. Thus, in 2010, the Korean government has decided to reduce the obesity rate down to 20% in adults and to 15% in youth, and is exploring ways to accurately define and diagnose obesity and metabolic diseases. To strategies for achieving objective, the government has been looking for the exact definition and measuring method about obesity and metabolic diseases.

Obesity drugs that are marketed inside and outside Korea include 'Xenical' (Roche Korea) with orlistat as main ingredient and approved by the FDA, 'Reductil' (Ilsung Pharmaceuticals) with sibutramine as main ingredient, 'Exolise' (Guju Pharma) with green tea catechol as main ingredient, or the like. Xenical, which reduces absorption of fat by inhibiting lipase, has the gastrointestinal-related side effects such as steatorrhea, gas generation and reduced absorption of oil-soluble vitamins. Reductil, which increases serotonin and noradrenaline levels in the sympathetic nervous system, has side effects such as headache, dry mouth, loss of appetite, insomnia, constipation, etc. Besides, a large number of anti-obesity drugs have been withdrawn from the market due to severe side effects. For example, aminophylline is reported to have various side effects in the nervous, circulatory and digestive systems despite its excellent effect of reducing body fat. Also, fenfluramine, dexfenfluramine, topiramate, ephedrine, etc. have been banned from being marketed as obesity drugs. As the synthetic drugs show limitations in side effects and in overcoming chronic diseases, foods and drugs derived from natural sources are drawing attentions.

NAFLD (non-alcoholic fatty liver disease) refers to a liver disease associated with triglyceride accumulation in the liver regardless of drinking alcohols, including steatosis and NASH (non-alcoholic steatohepatitis). Steatosis is considered benign diseases with good prognosis in clinic, but NASH accompanied with fatty liver, inflammation or fibrosis is recognized as progressive liver diseases inducing cirrhosis or liver cancer.

The obesity and the insulin resistance are representative of risk factors for NAFLD. The risk factors of hepatic fibrosis progression are, for example, obesity (BMI>30), ratio of liver function parameters detected in serum (AST/ALT>1) and diabetes. Hepatitis C carriers having the non-alcoholic fatty liver would be progressed to liver cancer; and therefore there are emerging needs for prevention and treatment of non-alcoholic fatty liver. 69-100% of patients with non-alcoholic fatty liver have obesity and 20-40% of patients in obesity are accompanied with fatty liver. Especially, prevalence of liver disease in the male obesity patients is higher than obesity women patients. There has been reported that 3-30% of adults with normal weight as well as obesity patients have fatty liver diseases in the Western society. In Japan having similar diet patterns to Korea, the prevalence of non-alcoholic fatty liver is estimated to be approximately 20% and 1% of them is estimated to be NASH. Non-alcoholic fatty liver became problems in obese children as well as adults. 10-77% of obese children (inhabited in Europe, USA and Asia) show non-alcoholic fatty liver lesions, because the most important risk factor for non-alcoholic liver disease is obesity.

The pathogenesis of non-alcoholic fatty liver may be explained by two mechanisms. The first mechanism is that the increase in free fatty acids inhibits fatty acid oxidation in hepatocytes, thereby accumulating fatty acids in hepatocytes to cause non-alcoholic fatty liver. The second mechanism involves a variety of physiological factors associated with inflammation and fibrosis progression. More specifically, the increase in levels of fatty acid induces to elevate the expression of cytochrome peroxidase 2E1 and CYP2E1 and to generate reactive oxygen species resulting in lipid peroxidation of liver cell membrane and the increase in LPS and oxidative stress, increasing the level of TNF-α being responsible for apoptosis of hepatocytes, finally inducing liver damage. The insulin resistance and the accumulation of fatty acids contribute to mitochondrial dysfunction, and the latter increases reactive oxygen species and nitric oxide synthase (NOS), thereby inducing cell death.

The best way to treat NAFDL may be considered a weight loss through lifestyle changes (e.g., the exercise). However, when it is difficult to treat NAFDL with only exercise, chemotherapeutics may be combined with exercise. Chemotherapeutics for non-acoholic fatty liver are classified: First, there are drugs with remediation of risk factors for treating and improving fatty liver, including obesity drugs (e.g., orlistat), insulin resistance drugs (e.g., metformin, pioglitazone and rosiglitazone), and hyperlipidemia drugs (e.g., clofibrate, gemfibrozil, bezafibrate, atorvastatin and simvastatin). Metformin increases oxidation of fatty acids, decreases lipogenic enzymes and improves hyperinsulinism and insulin resistance. Meanwhile, thiazolidinedione, rosiglitazone and pioglitazone are capable of activating PPARγ as nuclear hormone receptors to promote the glucose uptake in muscles. Secondly, there are drugs with potentials to recover liver cell damage being independent on remediation of risk factors of non-alcoholic fatty liver, including hepatocyte protectors (e.g., ursodeoxycholoc acid and taurine), antioxidants (e.g., Vitamins E and C), and nutritional supplements (e.g., lecithin, betaine, and N-acetylcysteine).

Unfortunately, there are no more plausible drugs with excellent therapeutic effects without adverse effects.

Nonenal contained in Garden Rocket [*Eruca sativa* Miller, *Eruca vesicaria sativa* (Mill.) Thell., *Eruca vesicaria* subsp. *sativa* (Mill.) Thell.] and Lovage [*Levisticum officinale* WDJ Koch., *Hipposelinum levisticum* (L.), *Levisticum officinalis, Levisticum paludapifolium* Asch., *Ligusticum levisticum* L.] is one of aldehyde compounds, which is also named as 3-hexyl-2-propenal, 3-hexylacrolein, heptylideneacetaldehyde, β-hexylacrolein, α-nonenyl aldehyde, nonylenic aldehyde and trans-2-nonenal (trans-2-nonenal).

Nonenal has the molecular formula of $C_9H_{16}O$ and the molecular weight of 140.22 g/mol, represented by the following chemical formula:

Nonenal has been used as flavoring agents or spices such as watermelon, oriental melon and melon scent, and registered in the food additives database of Domestic Food Code in Korea. It is also registered as flavoring agents in the U.S. FDA. It has been also reported to have microbial growth inhibitory effects (Trombetta D. et al., *Letters In Applied Microbiology*, 35(4):285-90 (2002)).

Nonenal is an edible substance with a significant high safety. It is noteworthy that the reported $LD_{50}$ of nonenal is more than 5,000 mg/kg (rats) (Joint FAO/WHO expert committee on food addictives, Sixty-third meeting, Geneva, 8-17, June 2004).

Throughout the specification, a number of publications and patent documents are referred to and cited. The disclosure of the cited publications and patent documents is incorporated herein by reference in its entirety to more clearly describe the state of the related art and the present disclosure.

SUMMARY OF THE INVENTION

The present inventors have made intensive studies to develop natural substance or compounds derived from natural substance having therapeutic efficacies for metabolic diseases including obesity, diabetes, dyslipidemia and non-alcoholic fatty liver. As a result, they have found out that nonenal is significantly effective in prevention or treatment of the metabolic diseases.

Accordingly, it is an object of this invention to provide a composition for preventing or treating obesity, diabetes, dyslipidemia, non-alcoholic fatty liver or insulin resistance syndrome.

It is another object of this invention to provide a method for preventing or treating obesity, diabetes, dyslipidemia, non-alcoholic fatty liver or insulin resistance syndrome.

Other features and aspects will be apparent from the following detailed description, drawings and claims.

BRIEF DESCRIPTION OF THE DRAWINGS

FIG. 4 shows visceral fat-pad weight (g) of mice fed with test diets. The results are represented as mean±SEM (standard error) of values obtained from eight mice. The characters above the bars indicate significant difference among dietary groups by one-way analysis of variance (ANOVA) test and Duncan's multiple range test (P<0.001).

FIGS. 6 and 7 show changes of biochemical indicators for obesity in blood of mice fed with nonenal. The results are represented as mean±SEM (standard error) of values obtained from eight mice. The characters above the bars indicate significant difference among dietary groups by one-way analysis of variance (ANOVA) test and Duncan's multiple range test (P<0.05).

FIG. 8 shows lipid levels in liver tissue of mice fed with nonenal. The results are represented as mean±SEM (standard error) of values obtained from eight mice. The characters above the bars indicate significant difference in dietary groups by one-way analysis of variance (ANOVA) test and Duncan's multiple range test (P<0.001).

FIG. 9 represents the expression profiles of genes relating to adipocyte differentiation in mice visceral fat tissues. The left panel represents images of RT-PCR analysis results for PPARγ2, C/EBPα, and aP2, and the right panel represents relative expression levels of these genes. The data were normalized to GAPDH mRNA levels and expressed as relative values to those from ND mouse. The results are represented as mean±SEM (standard error) of values obtained from eight mice. The characters above the bars indicate significant difference in dietary groups by one-way analysis of variance (ANOVA) test and Duncan's multiple range test (P<0.05).

DETAILED DESCRIPTION OF THE INVENTION

In one aspect of the present invention, there is provided a composition for preventing or treating metabolic diseases such as obesity, diabetes, dyslipidemia, fatty liver and insulin resistance syndrome (preferably, dyslipidemia or fatty liver, more preferably hyperlipidemia or non-alcoholic fatty liver).

In another aspect of the present invention, there is provided a method for preventing or treating metabolic diseases such as obesity, diabetes, dyslipidemia, fatty liver and insulin resistance syndrome (preferably, dyslipidemia or fatty liver, more preferably hyperlipidemia or non-alcoholic fatty liver) comprising: administering to a mammalian subject in need thereof a therapeutically effective amount of a composition comprising nonenal.

The present inventors have made intensive studies to develop natural substance or compounds derived from natural substance having therapeutic efficacies for metabolic diseases including obesity, diabetes, dyslipidemia and non-alcoholic fatty liver. As a result, they have found out that nonenal is significantly effective in prevention or treatment of the metabolic diseases.

According to the present invention, nonenal contributes to decrease in visceral fat-pad weights and levels of plasma lipids such as triglyceride, total cholesterol, LDL+VLDL cholesterol and free fatty acids as wells as plasma glucose level as demonstrated in Examples. In addition, nonenal significantly affects lipid level of liver tissues and liver function parameters as demonstrated in Examples.

According to the present invention, nonenal induces decreases in body weight, visceral fat, levels of plasma lipids such as triglyceride, total cholesterol and free fatty acid, and triglyceride level of liver tissues, thereby considerably alleviating obesity induced by HFD (high-fat diet). Furthermore, the gene expressions of both nuclear transcription factors and their target gene which are increased by obesity induced with HFD, are decreased by nonenal administration and the gene expressions of TNF-α and IL-6 are also decreased significantly to attenuate inflammatory responses in progressive non-alcoholic fatty liver.

As used herein, the term "fatty liver" refers to a condition where fat accumulates excessively in liver cells due to the disorder of lipid metabolism. It may cause various diseases such as angina, myocardial infarction, stroke, arteriosclerosis and pancreatitis.

As used herein, the term "diabetes" refers to a chronic disease characterized by relative or absolute lack of insulin, leading to glucose intolerance. As used herein, the term diabetes includes all kinds of diabetes, such as type 1 diabetes, type 2 diabetes and genetic diabetes. Type 1 diabetes, which is insulin-dependent diabetes, mainly results from the destruction of β-cells. Type 2 diabetes, which is non-insulin-dependent diabetes, is caused by insufficient secretion of insulin after meals or by insulin resistance.

As used herein, the term "insulin resistance" refers to a condition in which the natural hormone insulin becomes less effective at lowering blood sugars. When insulin resistance is high, the human body creates too much insulin to result in developments of not only hypertension and dyslipidemia but also heart diseases and diabetes. Especially, in type 2 diabetes, the increase in insulin is unrecognized in muscle and fat tissue, such that insulin action does not occur.

As used herein the term "insulin resistance syndrome" refers to a general term for disease which is induced by insulin resistance. It is characterized by cell resistance against insulin action, hyperinsulinemia, increase of very low density lipoprotein (VLDL) and triglyceride, decrease of high density lipoprotein (HDL) and hypertension. The insulin resistance syndrome is usually considered as a risk factor for cardiovascular disease and type 2 diabetes (Reaven G M, Diabetes, 37:1595-607 (1988)). In addition, it has been reported that insulin resistance increases intracellular oxidative stress together with risk factors such as hypertension, diabetes and smoking, and alters signal transduction to cause inflammatory responses, such that atherosclerosis is developed (Freeman B A. Et al., Lab Invest. 47: 412-26, (1982)), Kawamura M. et al, J Clin Invest. 94: 771-8 (1994)).

As used herein the term "metabolic diseases" refer to a group of a wide variety of diseases caused by risk factors for various cardiovascular diseases and type 2 diabetes, including insulin resistance and its related diverse and complicated metabolic and clinical abnormalities. In 1988, Reaven suggested that a common cause of these symptoms is insulin resistance and named insulin resistance syndrome; however, in 1998, WHO newly introduced the term "metabolic syndrome or metabolic diseases", because insulin resistance may not explain all the elements of these symptoms.

The composition of the present invention comprising nonenal as an active ingredient has activity for preventing diverse diseases of metabolic diseases such as obesity, diabetes, hyperlipemia, non-alcoholic fatty liver or insulin resistance syndrome. The composition of the present invention may prevent or treat metabolic diseases by its various action mechanisms.

As used herein the term "hyperlipidemia" refers to a disease caused by higher level of blood lipids due to poor metabolism of lipids such as triglyceride and cholesterol. More specifically, hyperlipidemia is characterized by increased levels of lipids such as triglyceride, LDL cholesterol, phospholipids and free fatty acids in blood, including hypercholesterolemia and hypertriglyceridemia.

According to a preferred embodiment, the insulin resistance syndrome treated by the present invention comprises obesity, hypertension, atherosclerosis, hyperlipidemia, hyperinsulinemia, non-alcoholic fatty liver and type 2 diabetes.

According to a preferred embodiment, the composition of the present invention decreases levels of blood fat, liver fat or visceral fat.

The term "liver" or "visceral" is used to encompass organ, tissue and cell.

As addressed in Examples, the groups fed with the composition of the present invention showed significantly reduced lipid level in blood and liver tissues, and the total visceral fat weight was significantly reduced by 59% as compared to HFD.

According to a more preferred embodiment, the fat reduced by the present invention comprises triglyceride, cholesterol and free fatty acid.

According to a more preferred embodiment, the visceral fat reduced by the present invention comprises epididymal fat, perirenal fat, mesenteric fat and/or retroperitoneal fat.

According to a preferred embodiment, the composition of the present invention decreases activity of ALT (alanine aminotransferase) or AST (aspartate aminotransferase).

ALT and AST as indicators for liver function are enzymes exhibiting increased levels in blood upon damage of liver.

The composition of the present invention significantly reduced both ALT (by 28%) and AST (by 31%) in the blood as compared to HFD-fed groups, addressing that nonenal has the excellent efficacies of improving fatty liver, preferably non-alcoholic fatty liver.

According to a preferred embodiment, the composition of the present invention decreases the expression of PPARγ (Peroxisome proliferator activated receptor gamma), C/EBPs (CCAAT enhancer-binding proterins) or aP2 (fatty acid binding protein). The composition of the present invention decreases the expression of not only PPARγ and C/EBPs but also aP2 as their target gene, finally decreasing amount of visceral fat. The aP2 gene is expressed during preadipocyte proliferation and differentiation to adipocytes and its expression is regulated by PPARγ and C/EBPs.

According to a preferred embodiment, the composition of the present invention decreases the expression of TNF-α (tumor necrosis factor-alpha) and IL-6 (interleukin-6).

It has been reported that when obesity is induced by HFD, free fatty acids (especially saturated fat) in body fluids are increased. The free fatty acids as ligands bound to TLR4 activate IKK and then NF-κB, and stimulate the secretion of pro-inflammatory cytokines such as TNF-α and IL-6 to cause inflammatory response. In addition, TNF-α and IL-6 activate both the cytokine signaling 3 (SOCS3) and JNK and induce phosphorylation of serine residues of insulin receptor substrates (IRS) to inhibit glucose transport, finally causing insulin resistance in peripheral tissues of liver or muscle.

According to a preferred embodiment, the composition of the present invention decreases glucose level in blood.

As demonstrated in Examples, the composition of the present invention significantly reduced fasting blood sugar level (by 31%) to improve insulin resistance, thereby exhibiting therapeutic efficacies for metabolic diseases.

According to a preferred embodiment, nonenal used in the present invention is derived from plants. Nonenal may be extracted or fractionated from plants such as garden Rocket (*Eruca sativa* Miller) and Lovage (*Levisticum officinale*).

Nonenal may be extracted from several plants or chemically synthesized in a mass production manner.

According to a preferred embodiment, the composition of the present invention is a pharmaceutical composition.

When the composition of the present disclosure is prepared as a pharmaceutical composition, the pharmaceutical composition of the present disclosure may comprise a pharmaceutically acceptable carrier. The pharmaceutically acceptable carrier included in the pharmaceutical composition of the present disclosure is one commonly used in the preparation of formulations and includes lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable excipients and formulations are described in detail in Remington's Pharmaceutical Sciences (19th ed., 1995).

The pharmaceutical composition of the present disclosure may be administered orally or parenterally. Preferably, it may be administered parenterally.

An appropriate administration dosage of the pharmaceutical composition of the present disclosure may be determined variously depending on such factors as preparation method, administration method, age, body weight and gender of a patient, pathological condition, diet, administration time, administration route, excretion rate or response sensitivity. Specifically, a daily dosage of the pharmaceutical composition of the present disclosure may be 0.001-100 mg/kg.

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

According to a preferred embodiment, the composition of the present invention is a food composition.

When the composition of the present disclosure is prepared as a food composition, the food composition of the present disclosure may comprise, in addition to nonenal of the present disclosure as the active ingredient, ingredients commonly added for preparation of food. For example, proteins, carbohydrates, fats, nutrients, seasoning or flavors may be added. The carbohydrate may be, for example, a sugar such as a monosaccharide, e.g. glucose, fructose, etc., a disaccharide, e.g. maltose, sucrose, oligosaccharide, etc. or a polysaccharide, e.g. dextrin, cyclodextrin, etc. or a sugar alcohol such as xylitol, sorbitol, erythritol, etc. The flavor may be a natural flavor [thaumatin, stevia extract (e.g. rebaudioside A, glycyrrhizin, etc.)] or a synthetic flavor (saccharin, aspartame, etc.).

For example, when the food composition of the present disclosure is prepared as a drink, it may further comprise, in addition to nonenal of the present disclosure as the active ingredient, citric acid, high-fructose corn syrup, sugar, glucose, acetic acid, malic acid, fruit juice, eucommia extract, jujube extract, licorice extract, or the like.

The features and advantages of the present invention may be summarized as follows:

(a) The present composition containing nonenal as an active ingredient is very effective in preventing or treating obesity, diabetes, dyslipidemia, fatty liver or insulin resistance syndrome (preferably, dyslipidemia or fatty liver, more preferably hyperlipidemia or fatty liver).

(b) Nonenal as active ingredients for the present composition may be isolated from various plants and chemically synthesized.

(c) The composition of the present invention useful as pharmaceuticals compositions or functional food compositions has therapeutic efficacies for obesity, diabetes, hyperlipidemia or fatty liver, and also induces significant decrease in fasting glucose level and blood insulin level to improve type 2 diabetes, insulin resistance and related metabolic disorders.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Reduction of Body and Visceral Fat-Pad Weights by Nonenal

1) Preparation of Test Diets and Maintenance of Test Animals

The obesity-inducing control diet used in the test was high-fat diet (HFD: 40% fat calorie, 17 g lard+3% corn oil/100 g diet). Diets supplemented with nonenal (nonenal-supplemented high fat diet, NED) had the same composition as HFD, except that nonenal was included at 0.2% (see Table 1). The normal diet group (Chow) was fed with commercially available rodent chow. Nonenal was purchased from Sigma-Aldrich.

TABLE 1

Compositions of test diets

| Ingredients | High-fat diet (HFD) (g/kg diet) | Nonenal-supplemented diet (NED) (g/kg diet) |
| --- | --- | --- |
| Casein | 200 | 200 |
| D/L-Methionine | 3 | 3 |
| Corn starch | 111 | 109 |
| Sucrose | 370 | 370 |
| Cellulose | 50 | 50 |
| Corn oil | 30 | 30 |
| Lard | 170 | 170 |
| Vitamin complex | 12 | 12 |
| Mineral complex | 42 | 42 |
| Choline bitartrate | 2 | 2 |
| Cholesterol | 10 | 10 |
| Tert-butylhydroquinone | 0.04 | 0.04 |
| nonenal | — | 2 |
| Total (g) | 1,000 | 1000 |
| Fat (% calorie) | 39.0 | 39.0 |
| Total calorie (kJ/kg diet) | 19,315 | 19,315 |

5-week-old male C57BL/6J mice (Orient, Korea) were accustomed to the laboratory environment for 1 week while feeding solid feed. Then, they were randomly divided into normal diet, high-fat diet and test groups and bred for a total of 10 weeks. The diet was given between 10 and 11 a.m. every day together with water. Food intake was measured every day and body weight was measured once a week. In order to avoid transient body weight increase after feed intake, body weight was measured 2 hours after removing the feed. After fasting the test animal for at least 12 hours and anesthetizing with diethyl ether, blood, liver and visceral fat (epididymal fat, perirenal fat, mesenteric fat and retroperitoneal fat) were taken and weighed after washing with 0.1 M PBS (pH 7.4). Blood taken from the abdominal aorta was centrifuged at 1000×g for 15 minutes for the separation of plasma.

2) Changes of Body and Visceral Fat-Pad Weights

Figure 1:
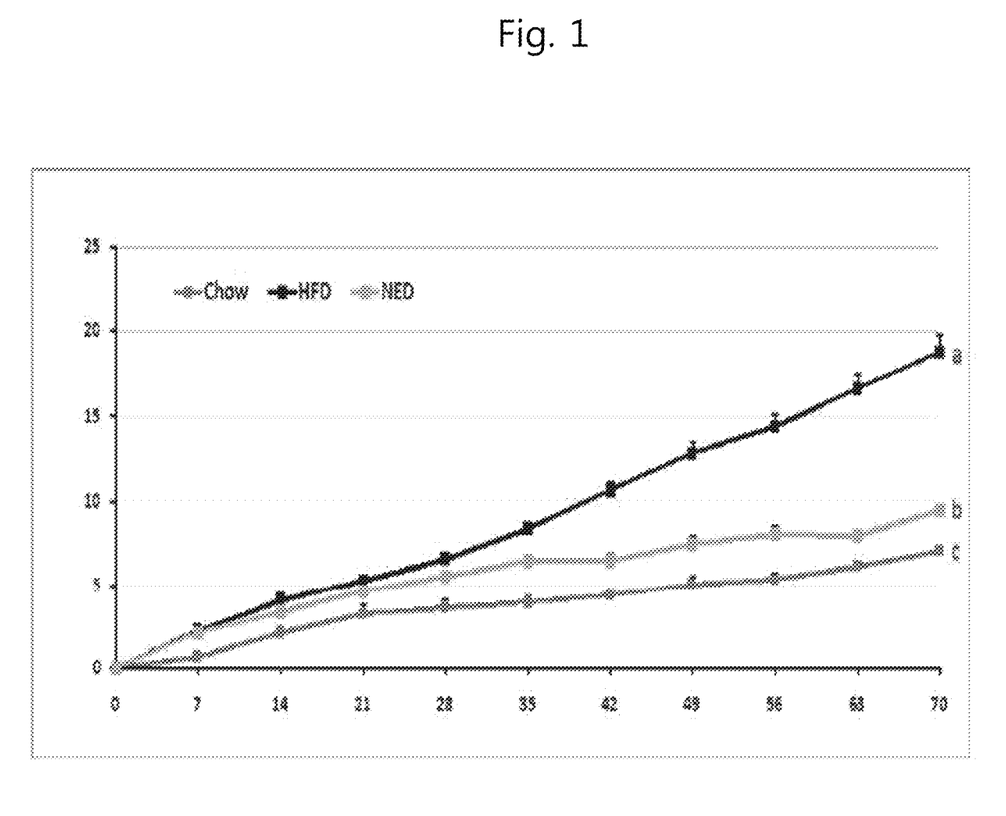
FIGS. 1-3 represent changes of body weight gain (g) in mice fed with test diets over time (x axis represents maintenance day) (FIG. 1), accumulated body weight gain for 10 weeks (g/70 days) (FIG. 2) and daily food intake (g/day) (FIG. 3), respectively. The results are represented as mean±SEM (standard error) of values obtained from eight mice. The characters above the bars indicate significant difference among dietary groups by one-way analysis of variance (ANOVA) test and Duncan's multiple range test (P<0.001).
Figure 2:
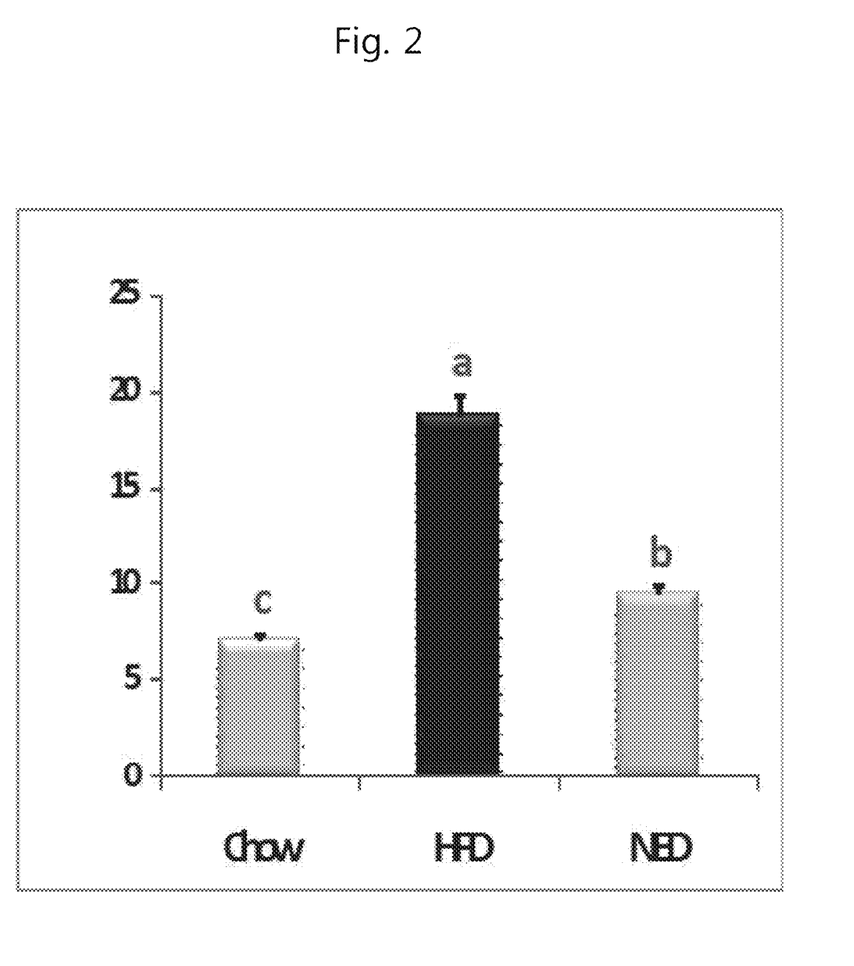
Figure 3:
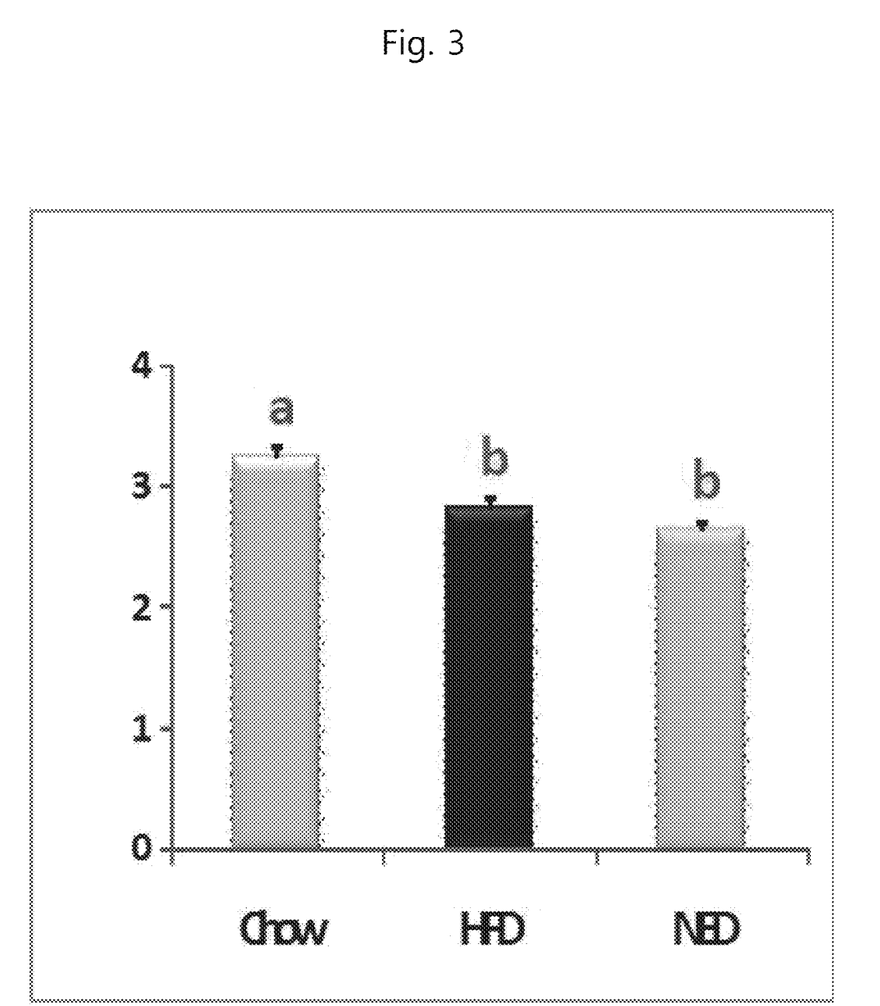

After feeding the test diet for 10 weeks, the nonenal-supplemented group showed significant decrease of body weight gain by 49% as compared to HFD. The dietary supplementation with nonenal induced no significant change in daily food intake (FIG. 3). Therefore, it would be understood that the body weight-decreasing effect by nonenal is not due to the suppression of appetite.

Figure 4:
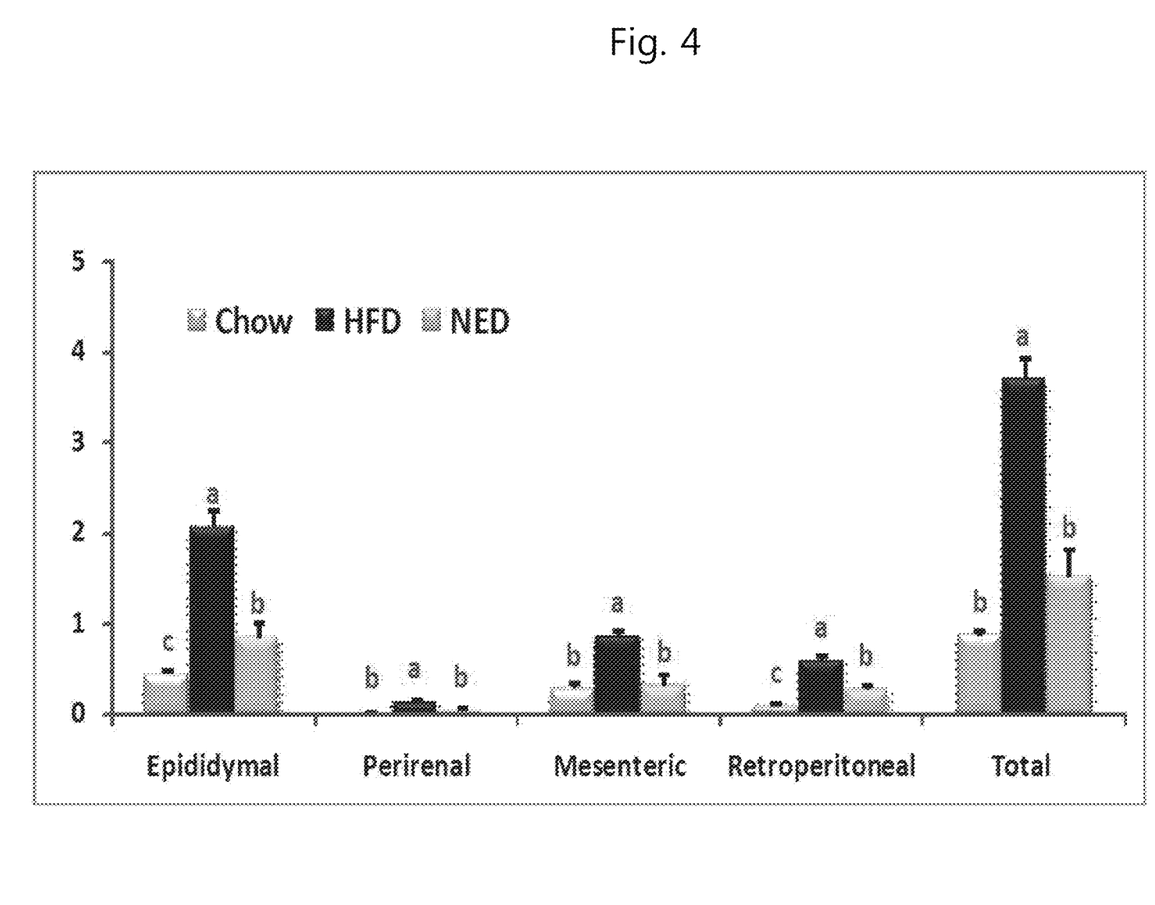
Figure 5:
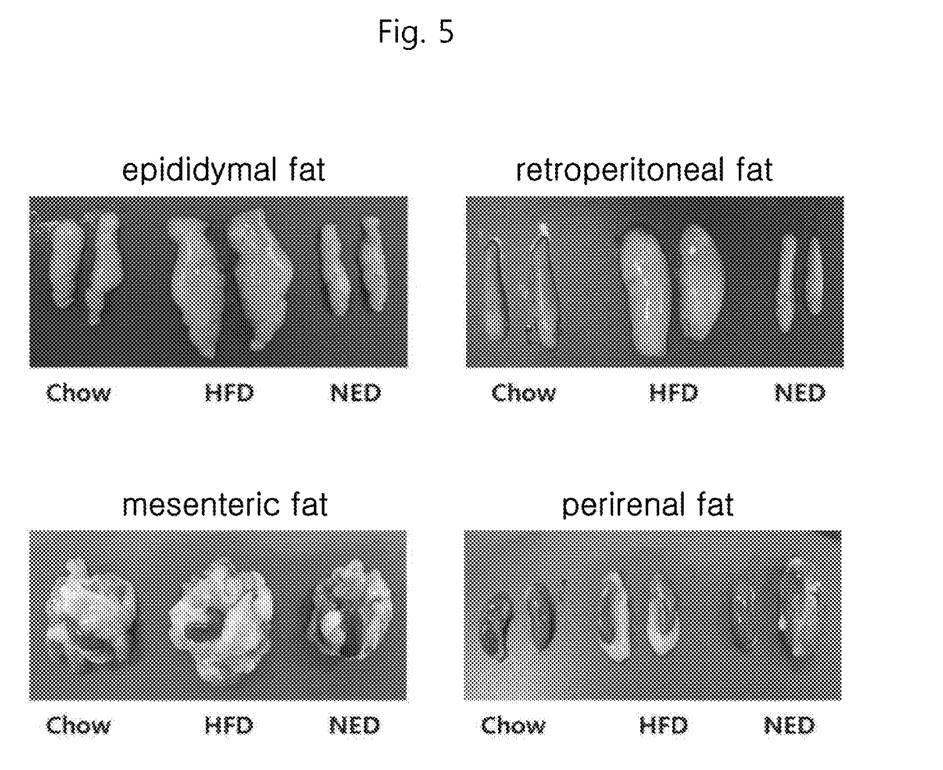
FIG. 5 represents images of visceral fat tissues of mice fed with test diets.

After feeding the test diet for 10 weeks, the epididymal, perirenal, mesenteric, and retroperitoneal fat-pads contained in the visceral fat were removed and weighed. The nonenal-supplemented group showed significantly reduced weights of the epididymal, perirenal, mesenteric, and retroperitoneal fat-pads as compared to HFD. The total visceral fat weight was significantly reduced by 59% in the NED group than in the HFD group (FIGS. 4 and 5). Accordingly, it would be appreciated that nonenal has excellent effects to reduce body weights and visceral fat-pad weights.

Example 2

Prevention and Treatment of Hyperlipidemia and Type 2 Diabetes by Nonenal

1) Biochemical Analysis of Blood

After 10 weeks of breeding, total cholesterol, triglyceride and glucose levels in the plasma and lipid levels in the liver tissue were measured as follows. Total cholesterol, triglyceride, free fatty acid and glucose levels in the plasma were measured twice for each using a commercially available kit (Bio Clinical System). The activity of ALT (alanine aminotransferase) and AST (aspartate aminotransferase) used as liver function indicator were measured twice for each using a commercially available kit (Bio Clinical System, Korea).

2) Changes of Plasma Lipid and Glucose Levels

Figure 6:
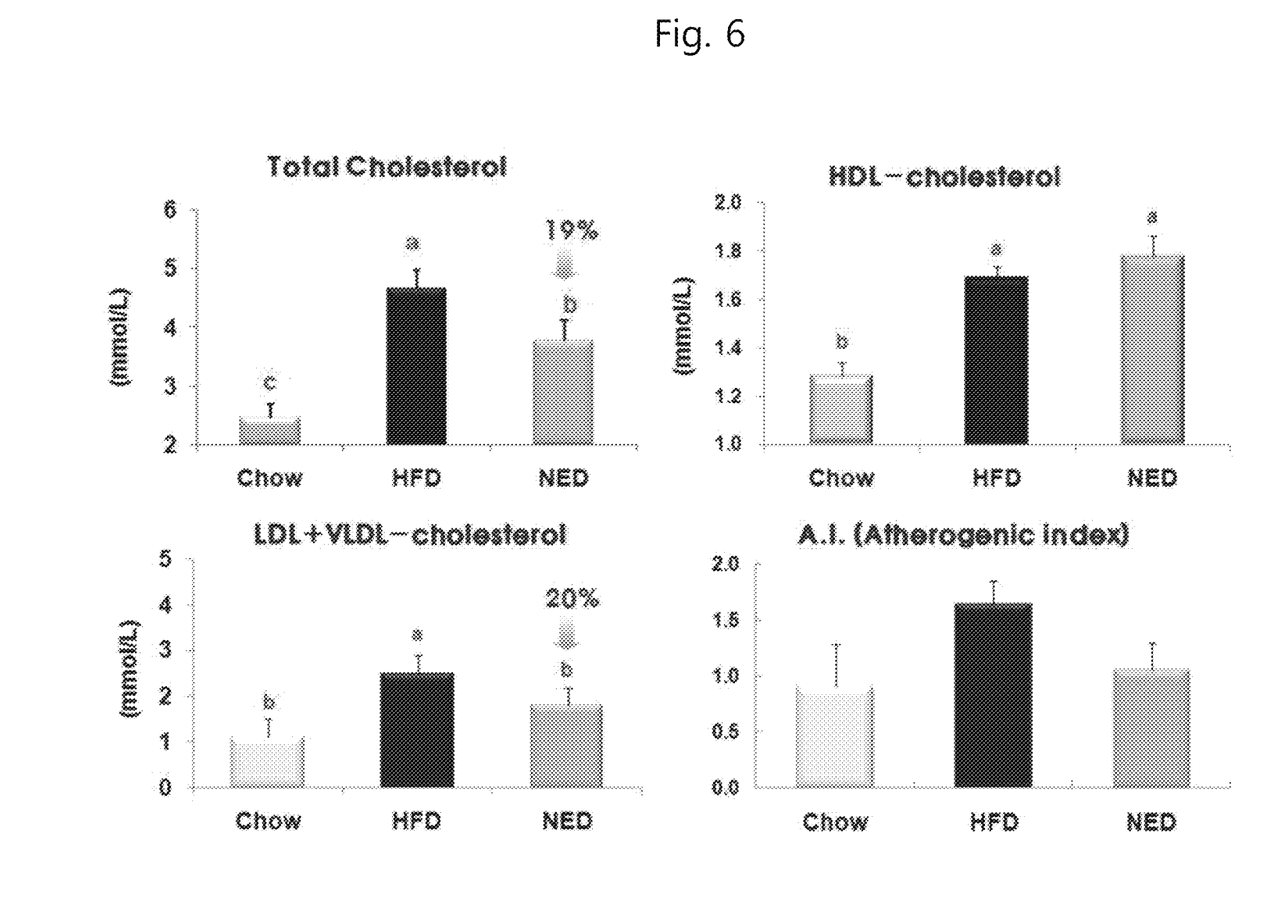
Figure 7:
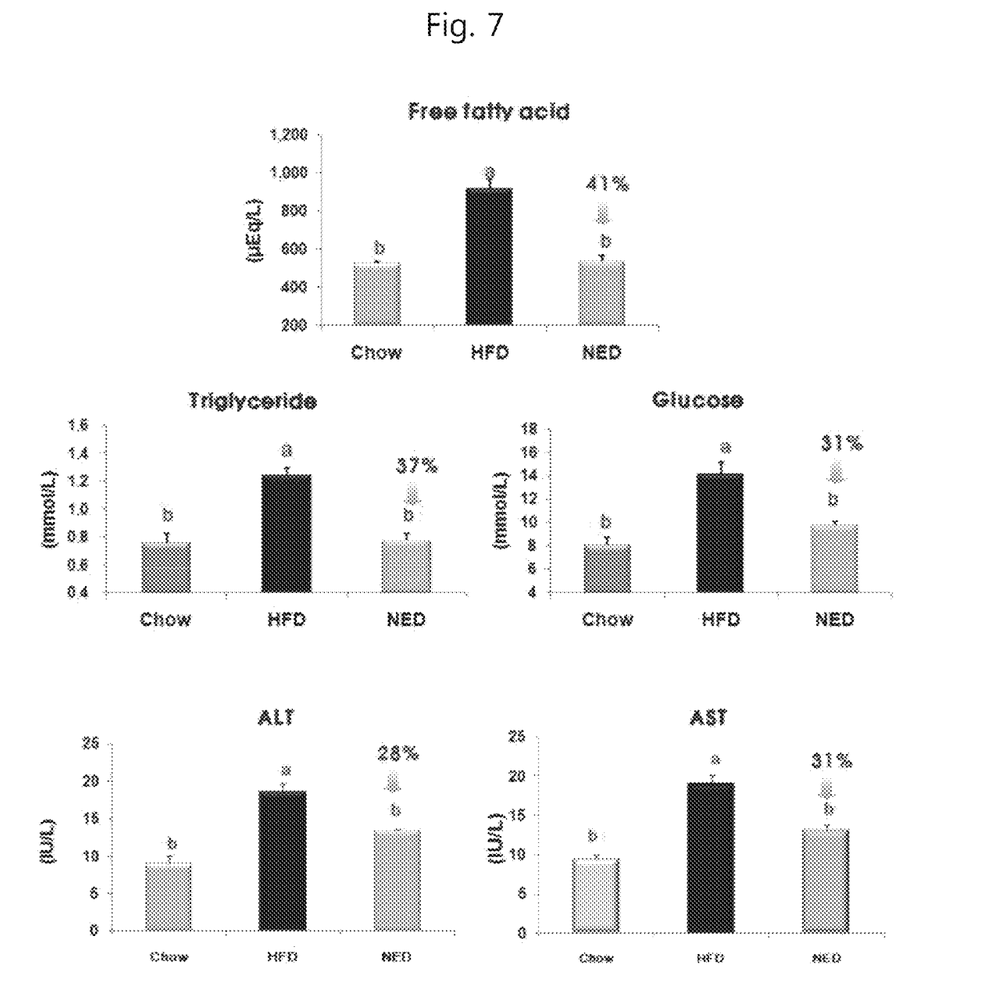
Figure 8:
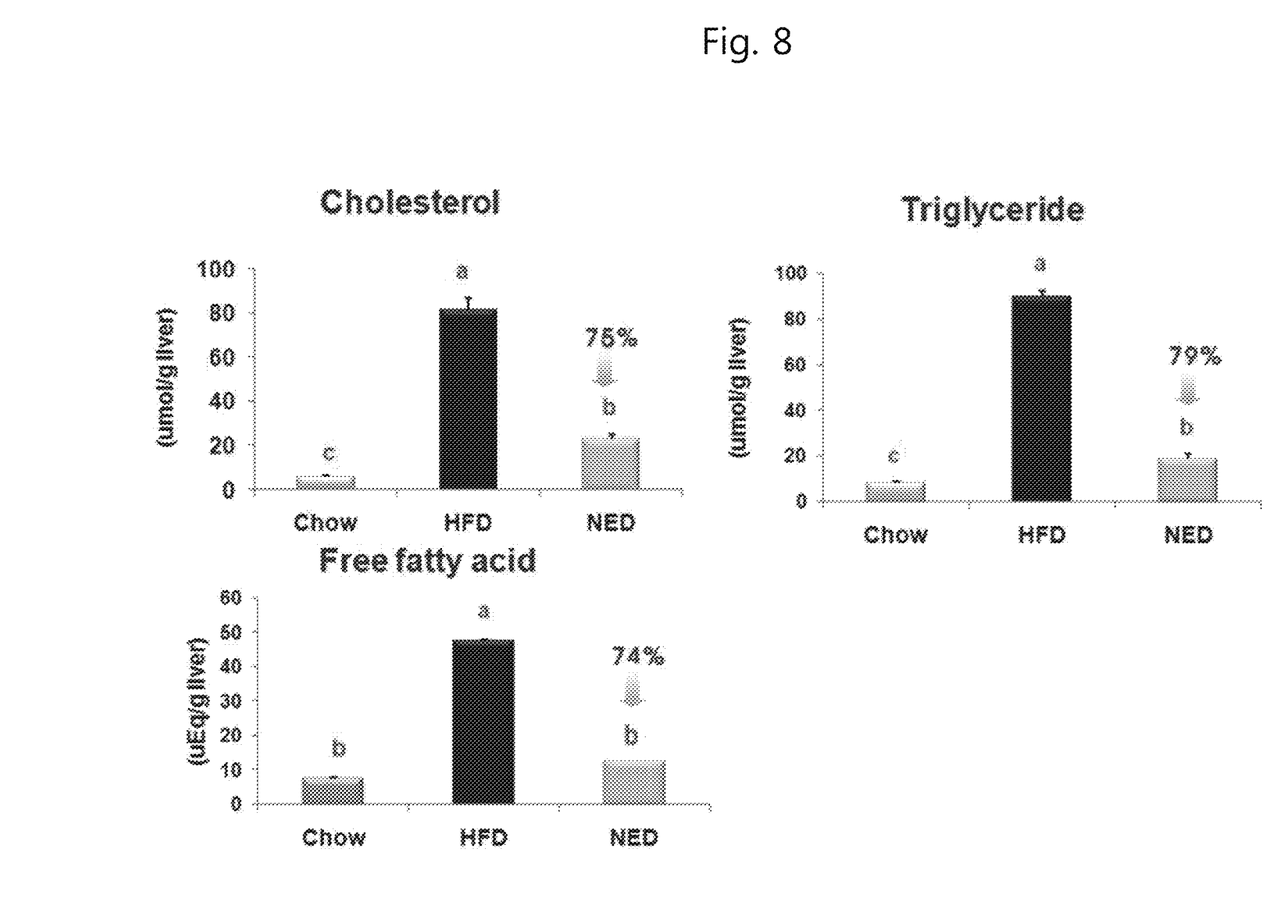

After feeding the test diet for 10 weeks, the nonenal-supplemented group showed significantly lower plasma levels of triglyceride (by 37%), total cholesterol (by 19%), LDL+VLDL cholesterol (by 20%), and free fatty acid (by 41%) as compared to the HFD group (FIGS. 6 and 7). Moreover, nonenal supplemented to the HFD resulted in a significant reduction of the fasting blood sugar level by 31%, as compared to HFD (FIG. 7). The HFD group exhibited significantly higher plasma activities of ALT (alanine aminotransferase) and AST (aspartate aminotransferase), which are parameters for hepatic function, as compared to the normal diet group and the NED group showed significantly decreased plasma activities of ALT (by 28%) and AST (by 31%) as compared to the HFD group. Accordingly, it could be recognized that nonenal has the excellent effects of improving hyperlipidemia, fasting blood sugar level, and hepatic function parameters in obesity induced by the HFD.

Example 3

Prevention and Treatment of Non-Alcoholic Fatty Liver by Nonenal

1) Analysis of Lipid Level in Liver Tissues

Lipids were extracted from the liver tissue according to Folch et al.'s method Folch J et al., J Biol. Chem. 226: 497-509 (1957)). After adding 1 mL of distilled water to 0.25 g of liver tissue, the liver tissue was homogenized using a Polytron homogenizer (IKA-Werke GmbH & Co., Ultra-Turrax, Staufen, Germany). After adding 5 mL of chloroform:methanol solution (2:1, v/v) to the homogenate and mixing well, the mixture was centrifuged at 1000×g for 10 minutes. After adding 2 mL of chloroform:methanol solution (2:1, v/v) again to the supernatant, the same procedure was repeated to completely separate the lipid components of the liver. After adding 3 mL of chloroform:methanol:0.05% $CaCl_2$ (3:48:47, v/v/v) solution to the remaining pellets and mixing well for 1 minute, followed by centrifugation at 1000×g for 10 minutes, the resulting pellets were completely dried with nitrogen gas. The dried lipids were dissolved in 1 mL of methanol and then analyzed.

The same kit (Bio Clinical System) as that used for the plasma analysis was used to measure the triglyceride and cholesterol levels of the liver tissue.

2) Changes of Hepatic Lipid Levels

After feeding the test diet for 10 weeks, the nonenal-supplemented group showed significantly decreased levels of triglyceride (by 78%), cholesterol (by 75%) and free fatty acid (by 74%) in liver tissue as compared to HFD. Accordingly, it could be understood that nonenal has the excellent effect of significantly improving fatty liver in obesity induced by HFD.

Example 4

Regulation of Gene Expressions Visceral Fat Tissues by Nonenal

1) RNA Extraction and RT-PCR (Reverse Transcription-Polymerase Chain Reaction) Analysis After adding 1 mL of Trizol agent per 0.1 g of visceral fat tissues, the mixture was homogenized and centrifuged at 12,000×g for 10 min at 4° C. The supernatant was transferred to a new tube and 200 µl of chloroform was added to the tube, followed by vortexing. The same procedure was repeated twice and then the supernatant was transferred to a new tube, followed by addition of isopropanol and the supernatant at 1:1 ratio. The mixture was vigorously shaken 10 times and then incubated for 10 min at room temperature, followed by centrifugation at 12,000×g for 10 min at 4° C. to remove the supernatant. After adding 1 mL of 70% ethanol to the remaining pellet, it was centrifuged at 7,500×g for 5 min at 4° C. After removing the ethanol, the RNA pellet contained in the tube was dried for 5 min at 4° C. and dissolved in nuclease-free water. The RNA sample concentration was measured at a wavelength of 260 nm and 280 nm using a UV/VIS spectrophotometer (Beckman coulter, DU730) and the integrity of RNA sample was verified by agarose gel electrophoresis.

The RNA sample obtained from the visceral fat tissues was trasnscribed using oligo dT primer and SuperScript reverse transcriptase (GIBCO BRL, Gaithersburg, Md., USA) to synthesize cDNA. The PCR amplification was performed using the cDNA as templates and primers complementary to cDNA 5' and 3' flanking sequence. The sequences of the primers used are presented in Table 2. The amplified products were resolved on agarose gel electrophoresis.

TABLE 2

Primer sequences for RT-PCR

| Gene | Primer | Sequence (5'→3') | Annealing Temp (° C.) | Size of PCR product (bp) |
|---|---|---|---|---|
| Peroxisome proliferator activated receptor gamma (PPARγ2) | forward primer | TTCGGAATCAGCTCTGTGGA | 55 | 148 |
| | reverse primer | CCATTGGGTCAGCTCTTGTG | | |
| Fatty acid binding protein (aP2) | forward primer | AGCATCATAACCCTAGATGG | 55 | 128 |
| | reverse primer | GAAGTCACGCCTTTCATAAC | | |
| CCAAT/enhancer binding protein alpha (C/EBPα) | forward primer | TCGGTGCGTCTAAGATGAGG | 55 | 187 |
| | reverse primer | TCAAGGCACATTTTTGCTCC | | |
| TNFalpha (TNFα) | forward primer | TGTCTCAGCCTCTTCTCATT | 55 | 156 |
| | reverse primer | AGATGATCTGAGTGTGAGGG | | |
| Interleukin6 (IL-6) | forward primer | ATGAAGTTCCTCTCTGCAAGAGACT | 55 | 638 |
| | reverse primer | CACTAGGTTTGCCGAGTAGATCTC | | |
| Glyceraldehyde-3-phosphated ehydrogenase (GAPDH) | forward primer | AGAACATCATCCCTGCATCC | 55 | 321 |
| | reverse primer | TCCACCACCCTGTTGCTGTA | | |

2) Results of RT-PCR Analysis of Visceral Fat Tissues

Figure 9:
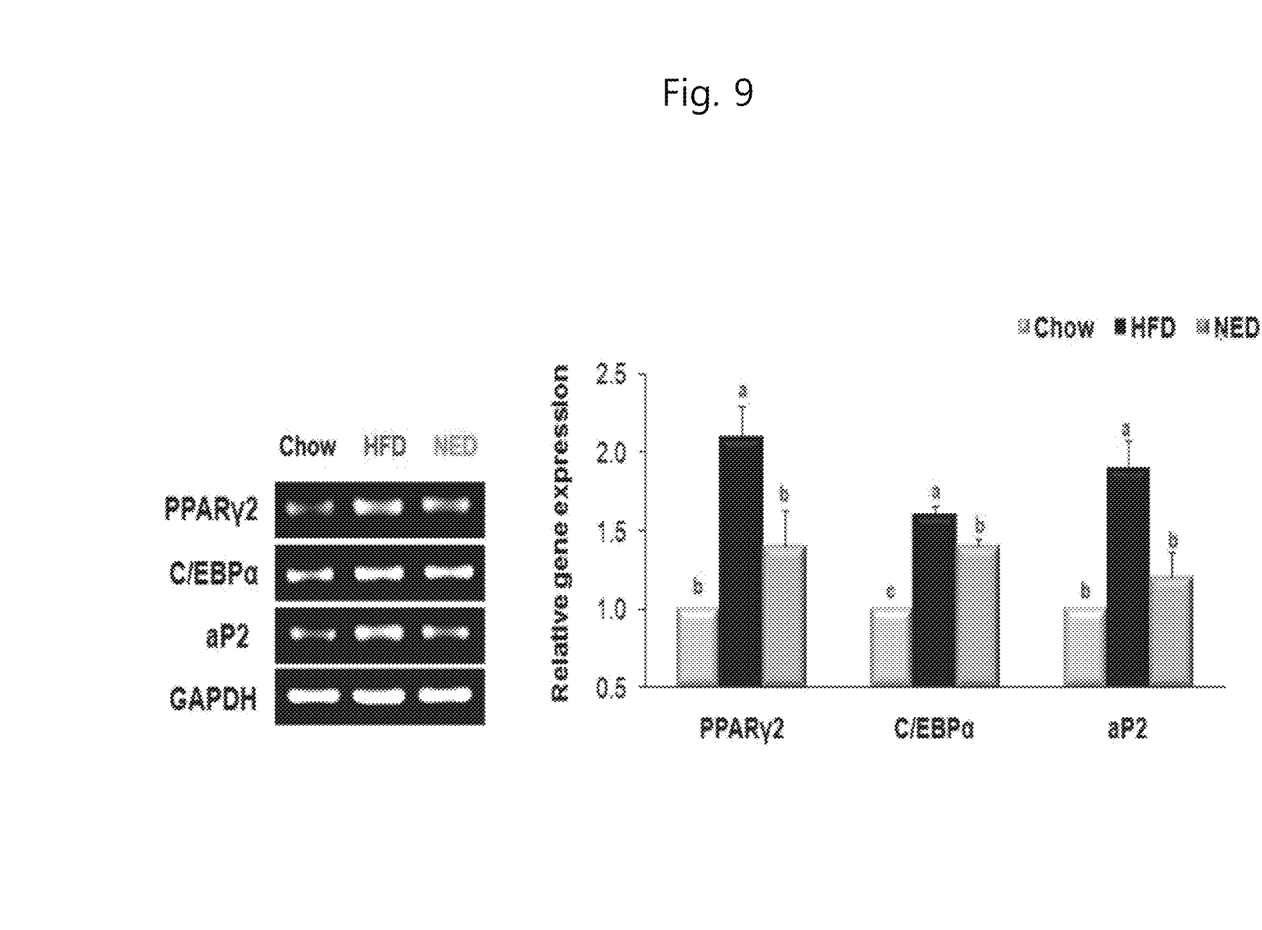

The mRNA expressions of visceral fat tissues were evaluated by RT-PCR analysis. The HFD group showed significantly increased expressions of C/EBPα, PPARγ2 and aP2 genes as compared to the Chow group. Nuclear transcription factors, C/EBPα and PPARγ2, play an important role in adipogenesis and aP2 is the target gene for these transcription factors. In contrast, nonenal supplemented to the HFD significantly decreased the expression of C/EBPα, PPARγ2 and aP2 genes to levels similar for the Chow group (FIG. 9). Accordingly, it could be understood that nonenal prevented HFD-induced accumulation of fat in the visceral adipose tissue by decreasing the expression of nuclear transcription factors and their target gene.

It was well known to one of skill in the art that diet-induced obesity animal models or obese humans exhibit Type 2 diabetes showing simultaneously elevated blood insulin and glucose levels in fasted state. A term "metaflammation" was recently coined to indicate inflammations induced by excess supply of nutrients or metabolites and obesity was indicated as chronic and low-level inflammation, highlighting the correlation between obesity and immune system. For example, the TLR4 (toll-like receptor 4) molecule responsible for innate immune responses plays a pivotal role in inflammation and insulin resistance pathway in response to dietary fats (particularly, saturated fatty acids) as ligands.

When obesity is induced by HFD, the free fatty acids (especially saturated fatty acids) in body fluids are increased. The free fatty acids as ligands bound to TLR4 activate IKK and then NF-κB, and stimulate the secretion of pro-inflammatory cytokines such as TNF-α and IL-6 to cause inflammatory response. In addition, TNF-α and IL-6 activate both the cytokine signaling 3 (SOCS3) and JNK and induce phosphorylation of serine residues of insulin receptor substrates (IRS) to inhibit glucose transport, finally causing insulin resistance in peripheral tissues of liver or muscle.

Figure 10:
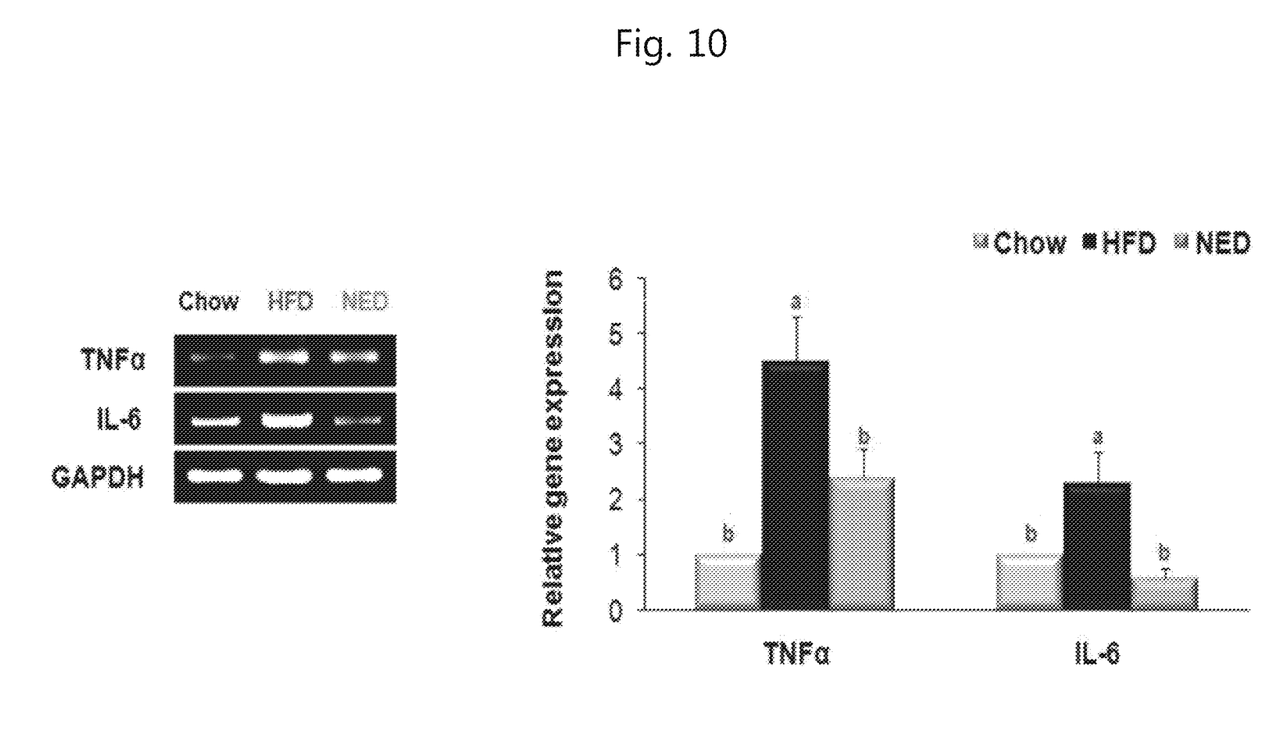
FIG. 10 shows change of gene expression profiles of pro-inflammatory cytokines in mice visceral fat tissues.

The mRNA expression profiles of pro-inflammatory cytokines in visceral fat tissues were evaluated using RT-PCR. The HFD group exhibited significantly higher levels of both TNF-α and IL-6 gene expressions as compared to the Chow group. Meanwhile, these HFD-induced elevations in the expression of TNF-α and IL-6 were significantly reversed by feeding nonenal (FIG. 10). Accordingly, it would be concluded that nonenal has the excellent effects of decreasing inflammatory responses in the visceral fat tissues.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

What is claimed is:

1. A method for treating hyperlipidemia or fatty liver, the method comprising:
   administering to a mammalian subject in need thereof a therapeutically effective amount of a composition comprising nonenal.

2. The method according to claim 1, wherein the composition decreases an amount of blood fat, liver fat or visceral fat in the mammalian subject.

3. The method according to claim 2, wherein the blood fat, liver fat, or visceral fat comprises triglyceride, cholesterol and free fatty acid.

4. The method according to claim 2, wherein the visceral fat is one or more selected from the group consisting of epididymal fat, perirenal fat, mesenteric fat and retroperitoneal fat.

5. The method according to claim 1, wherein the composition decreases activity of ALT (alanine aminotransferase) or AST (aspartate aminotransferase) in the mammalian subject.

6. The method according to claim 1, wherein the composition decreases expression of PPARγ (Peroxisome proliferator activated receptor gamma), C/EBPs (CCAAT enhancer-binding proterins) or aP2 (fatty acid binding protein) in the mammalian subject.

7. The method according to claim 1, wherein the composition decreases expression of TNF-α (tumor necrosis factor-alpha) and IL-6 (interleukin-6) in the mammalian subject.

8. The method according to claim 1, wherein the composition decreases a glucose level in blood of the mammalian subject.

9. The method according to claim 1, wherein the nonenal is derived from plants.

10. The method according to claim 1, wherein the composition is a pharmaceutical composition or food composition.

* * * * *